(12) United States Patent
Takeuchi et al.

(10) Patent No.: US 11,020,530 B2
(45) Date of Patent: Jun. 1, 2021

(54) SYRINGE BARREL FOR PRE-FILLED SYRINGE, SYRINGE SYSTEM, AND PRE-FILLED SYRINGE

(71) Applicant: TERUMO KABUSHIKI KAISHA, Tokyo (JP)

(72) Inventors: Katsuyuki Takeuchi, Tokyo (JP); Eiji Yagishita, Shizuoka (JP); Nobukazu Akaike, Shizuoka (JP); Koji Nakamura, Tokyo (JP); Tsutomu Ueda, Kanagawa (JP); Kimiya Mori, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 26 days.

(21) Appl. No.: 16/169,392

(22) Filed: Oct. 24, 2018

(65) Prior Publication Data

US 2019/0054241 A1 Feb. 21, 2019

Related U.S. Application Data

(63) Continuation of application No. PCT/JP2017/016416, filed on Apr. 25, 2017.

(30) Foreign Application Priority Data

Apr. 25, 2016 (JP) .............................. JP2016-086947

(51) Int. Cl.
*A61M 5/31* (2006.01)
*A61M 5/28* (2006.01)
(Continued)

(52) U.S. Cl.
CPC .......... *A61M 5/3129* (2013.01); *A61M 5/001* (2013.01); *A61M 5/002* (2013.01);
(Continued)

(58) Field of Classification Search
CPC .... A61M 5/3129; A61M 5/001; A61M 5/002; A61M 5/28; A61M 5/31; A61M 5/3202; A61M 2005/3131
See application file for complete search history.

(56) References Cited

U.S. PATENT DOCUMENTS 9,155,839 B1 10/2015 Willis et al.
2002/0088131 A1 7/2002 Baxa et al.
(Continued)

FOREIGN PATENT DOCUMENTS

CN 101968408 A 2/2011
CN 104162211 A 11/2014
(Continued)

OTHER PUBLICATIONS

International Searching Authority, "International Search Report," issued in connection with International Patent Application No. PCT/JP2017/016416, dated Aug. 1, 2017.
(Continued)

*Primary Examiner* — Nathan R Price
*Assistant Examiner* — Dung T Ulsh
(74) *Attorney, Agent, or Firm* — Foley & Lardner LLP (57) ABSTRACT

A syringe body for a prefilled syringe includes: a hollow body portion; a proximal-end opening portion provided at a proximal end portion of the body portion; and a distal-end nozzle provided at a distal end portion of the body portion. The body portion is made of a cyclic olefin polymer or a cyclic olefin copolymer. The body portion has a thick body portion accounting for 80% or more of the body portion along an axial direction. A wall thickness of the thick body portion is 2.23 to 2.40 mm.

13 Claims, 7 Drawing Sheets

(51) Int. Cl.
 *A61M 5/00* (2006.01)
 *A61M 5/32* (2006.01)
 *A61M 5/34* (2006.01)
 *B32B 25/08* (2006.01)

(52) U.S. Cl.
 CPC ............... *A61M 5/28* (2013.01); *A61M 5/31* (2013.01); *A61M 5/3202* (2013.01); *A61M 5/345* (2013.01); *A61M 2005/3131* (2013.01); *A61M 2205/0238* (2013.01); *B32B 25/08* (2013.01)

(56) References Cited

U.S. PATENT DOCUMENTS

| | | | |
|---|---|---|---|
| 2004/0054332 | A1 | 3/2004 | Ferguson |
| 2008/0033367 | A1* | 2/2008 | Haury ................. A61M 5/3129 604/187 |
| 2008/0156831 | A1* | 7/2008 | Nakayama ............... B32B 1/02 222/327 |
| 2008/0230961 | A1* | 9/2008 | Moesli .................... B29C 51/10 264/524 |
| 2008/0262435 | A1 | 10/2008 | Erickson et al. |
| 2011/0276005 | A1* | 11/2011 | Hioki ...................... B05D 1/02 604/187 |
| 2012/0123345 | A1* | 5/2012 | Felts .................... A61M 5/3129 604/187 |
| 2013/0168393 | A1* | 7/2013 | Nakano ................... C08J 5/121 220/200 |
| 2014/0110289 | A1* | 4/2014 | Geuder ............... A61F 9/00727 206/364 |
| 2017/0135900 | A1* | 5/2017 | Yano ........................ A61J 1/00 |

FOREIGN PATENT DOCUMENTS

| | | |
|---|---|---|
| EP | 2 216 061 A1 | 8/2010 |
| JP | H939042 A | 2/1997 |
| JP | 2004-229750 A | 8/2004 |
| JP | 2006-016053 A | 1/2006 |
| JP | 2008-272162 A | 11/2008 |
| JP | 2010-505668 A | 2/2010 |
| JP | 5325247 B2 | 10/2013 |
| JP | 2014-195516 A | 10/2014 |
| JP | 2015-073635 A | 4/2015 |
| WO | WO-2005/032619 A1 | 4/2005 |
| WO | WO-2009/057378 A1 | 5/2009 |
| WO | WO-2011/059823 A1 | 5/2011 |
| WO | WO-2016/002686 A1 | 1/2016 |

OTHER PUBLICATIONS

International Searching Authority, "Written Opinion," issued in connection with International Application No. PCT/JP2017/016416, dated Aug. 1, 2017.
Extended European Search Report dated Nov. 5, 2019 for corresponding European Patent Application No. 17789549.7.
Extended European Search Report dated Jan. 30, 2020 in European Patent Application No. 17789538.0.
"Prefilled syringes—Part 6: Plastic barrels for injectables"; International Standard—ISO 11040-6:2012(E); First Edition; Apr. 1, 2012.
Office Action dated Dec. 1, 2020 in counterpart Chinese Patent Application No. 201780022140.0.
Office Action dated Dec. 2, 2020 in related Chinese Patent Application No. 201780021837.6.

* cited by examiner

TABLE 1

MIGRATION AMOUNT OF HYDROGEN PEROXIDE

|  | ZEROTH DAY (INITIAL) | THIRD DAY | FOURTEENTH DAY |
|---|---|---|---|
| EXAMPLE A | N. D. | 0.02ppm | N. D. |
| COMPARATIVE EXAMPLE A | N. D. | 0.11ppm | 0.37ppm |

FIG. 7

TABLE 2

NUMBER OF VIABLE BACTERIA (AVERAGE WHEN N = 5)

|  | ZEROTH DAY (INITIAL) | FOURTEENTH DAY |
|---|---|---|
| EXAMPLE B | $4.02 \times 10^6$ | 0 |
| COMPARATIVE EXAMPLE B | $4.02 \times 10^6$ | $0.786 \times 10^6$ |

SYRINGE BARREL FOR PRE-FILLED SYRINGE, SYRINGE SYSTEM, AND PRE-FILLED SYRINGE

CROSS-REFERENCE TO RELATED APPLICATIONS

The present application is a bypass continuation of PCT Application No. PCT/JP2017/016416, filed on Apr. 25, 2017, which claims priority to Japanese Application No. 2016-086947, filed on Apr. 25, 2016. The contents of these applications are hereby incorporated by reference in their entireties.

BACKGROUND

The present disclosure relates to a syringe body for a prefilled syringe, a syringe system, and a prefilled syringe.

Conventionally, the following two methods are known as methods for sterilizing an outer surface of a prefilled syringe packed in a packaging container such as a blister package.

In a first method, a hydrogen peroxide solution is dripped into the packaging container to be packaged, and an outer surface of a syringe body of the prefilled syringe is sterilized with a hydrogen peroxide gas that is volatilized in the package. In a second method, a material having gas permeability is used for a part of the packaging container, and the outer surface of the syringe body of the prefilled syringe is sterilized with an ethylene oxide gas for each packaging container accommodating the prefilled syringe. In particular, the first method is often used in a prefilled syringe filled with 10 mL of a heparin preparation (JP 5325247 B2).

SUMMARY

In the above-described sterilizing methods, there is a case in which a sterilizing gas permeates through a syringe body made of plastic or the like to migrate into the syringe body so that a sterilizing medium remains in a drug solution. In a prefilled syringe of 10 mL, it is possible to minimize the amount of the sterilizing medium remaining in the drug solution in the plastic syringe body relative to the amount of the drug solution by adjusting aeration or the like at the time of sterilization.

However, in the case of a prefilled syringe with a small amount of the drug solution (for example, an amount in a range of 0.1 to 5 mL), there is a risk that the amount of the sterilizing medium remaining in the drug solution may be an amount that should not be ignored. In addition, when an active ingredient in the drug solution is liable to cause denaturation such as oxidation by the sterilizing medium, there is a risk that the active ingredient is denatured if the amount of the sterilizing medium that migrates to the drug solution increases even in a short period of time.

Meanwhile, a syringe body having a nominal volume of 1 mL and a thickness of 2.43 mm has been proposed as a syringe body made of a cyclic olefin polymer, which is one type of plastic or a cyclic olefin copolymer. However, when molding the syringe body having a thickness of 2.43 mm with the cyclic olefin polymer or the cyclic olefin copolymer, shrinkage, called a "sink mark" occurs at the time of molding, which may cause deviation in dimensions of the syringe body and lead to a liquid leakage or extreme deterioration of production efficiency due to a significant extension of a cooling step during the molding.

Therefore, an object of certain embodiments described in the present disclosure is to provide a syringe body for a prefilled syringe, a syringe system, and a prefilled syringe that can be produced with sufficient efficiency to cause few sink marks at the time of molding of the syringe body while minimizing migration of a sterilizing medium to a drug solution filling the syringe body when sterilizing an outer surface of the syringe body with a gas.

In one embodiment, a syringe body for a prefilled syringe includes: a hollow body portion; a proximal-end opening portion disposed at a proximal end portion of the body portion; and a distal-end nozzle disposed at a distal end portion of the body portion. The body portion is made of a cyclic olefin polymer or a cyclic olefin copolymer. The body portion has a thick body portion accounting for 80% or more of the body portion along an axial direction. A wall thickness of the thick body portion is in a range of 2.23 to 2.40 mm.

According to the syringe body configured as described above, the wall thickness of the thick body portion accounting for 80% or more of the body portion is appropriately as large as 2.23 to 2.40 mm, and thus, it is possible to effectively suppress the migration of a sterilizing medium into the syringe body when sterilizing the outer surface of the syringe body with a gas. Therefore, even when an active ingredient in the drug solution filling the syringe body is liable to cause denaturation such as oxidation, it is possible to suppress the denaturation of the active ingredient. In addition, although the body portion is made of the cyclic olefin polymer or the cyclic olefin copolymer, the wall thickness of the body portion is not too thick, and thus, it is possible to reduce the sink marks during molding at the time of molding the syringe body. Because the sink marks are reduced during molding, it is easy to secure proper dimensional accuracy of the syringe body, and it is possible to produce the syringe body with sufficient efficiency because the extension of time for the cooling step is avoided.

The nominal volume of the syringe body may be in a range of 0.1 to 5 mL.

When the nominal volume is in a range of 0.1 to 5 mL, the amount of a filling drug solution is small, and it is desirable to minimize the migration of the sterilizing gas into the syringe body, and thus, the thickness of the body portion employed in the present invention is advantageous.

The nominal volume of the syringe body may be in a range of 0.1 to 0.5 mL.

When the nominal volume is in a range of 0.1 to 5 mL, the amount of a filling drug solution is extremely small, and it is desirable to minimize the migration of the sterilizing gas into the syringe body, and thus, the thickness of the body portion employed in the syringe body is particularly advantageous.

The area of an outer circumferential surface of the body portion may be in a range of 1300 to 1600 $mm^2$.

As the contact area between the sterilizing gas and the outer circumferential surface of the body portion is set to be as small as possible, it is possible to decrease the amount of a sterilizing gas required for sterilizing the outer circumferential surface. As a result, it is possible to decrease the amount of a sterilizing gas migrating into the syringe body.

In another embodiment, a syringe system for a prefilled syringe includes: a syringe body that includes a hollow body portion, a proximal-end opening portion disposed at a proximal end portion of the body portion, and a distal-end nozzle disposed at a distal end portion of the body portion; a gasket configured to slide inside the body portion; and a cap that has a sealing portion sealing an opening portion of the distal-end nozzle. The body portion is made of a cyclic olefin polymer or a cyclic olefin copolymer, and a wall thickness of the body portion is in a range of 2.23 to 2.40 mm.

The nominal volume of the syringe body may be in a range of 0.1 to 5 mL.

The gasket may have a gasket body and a fluororesin disposed on an outer surface of the gasket body.

A gas barrier property is improved by the fluororesin, and the sterilizing gas is less likely to migrate into the syringe body.

The sealing portion of the cap may be made of butyl rubber.

Because the butyl rubber has low gas permeability, the sterilizing gas is less likely to migrate into the syringe body.

In another embodiment, a prefilled syringe includes: a syringe body that includes a hollow body portion, a proximal-end opening portion disposed at a proximal end portion of the body portion, and a distal-end nozzle disposed at a distal end portion of the body portion; a gasket that is slidably inserted into the body portion; a cap that has a sealing portion sealing an opening portion of the distal-end nozzle; and a drug solution that is filled in a filling space formed by the syringe body and the gasket. A nominal volume of the syringe body is in a range of 0.1 to 5 mL. The body portion is made of a cyclic olefin polymer or a cyclic olefin copolymer. A wall thickness of the body portion is in a range of 2.23 to 2.40 mm. An outer surface of the syringe body is sterilized with a hydrogen peroxide or ethylene oxide gas.

In another embodiment, a prefilled syringe includes: a syringe body that includes a hollow body portion, a proximal-end opening portion disposed at a proximal end portion of the body portion, and a distal-end nozzle disposed at a distal end portion of the body portion; a gasket that is slidably inserted into the body portion; a cap that has a sealing portion sealing an opening portion of the distal-end nozzle; and a drug solution that is filled in a filling space formed by the syringe body and the gasket. The body portion is made of a cyclic olefin polymer or a cyclic olefin copolymer. A wall thickness of the body portion is in a range of 2.23 to 2.40 mm. The drug solution is a medicine containing an active ingredient that is easily oxidized, an emulsion preparation, or a medicine that requires sterilization of an outer surface of the syringe body in order to prevent infection during clinical use. The outer surface of the syringe body is sterilized with a hydrogen peroxide or ethylene oxide gas.

The active ingredient may be a protein, a peptide, or a nucleic acid.

When the active ingredient is any one of these materials, the drug solution is particularly easily oxidized so that the thickness of the body portion employed in the syringe body is advantageous.

The nominal volume of the syringe body is in a range of 0.1 to 5 mL.

According to the syringe body for a prefilled syringe, the syringe system, and the prefilled syringe of the present invention, it is possible to perform the production with sufficient efficiency to cause few sink marks at the time of molding of the syringe body while minimizing the migration of the sterilizing medium to the drug solution filling the syringe body when sterilizing the outer surface of the syringe body with the gas.

DETAILED DESCRIPTION

Hereinafter, embodiments of a syringe body, a syringe system, and a prefilled syringe will be described with reference to the accompanying drawings.

Figure 1:
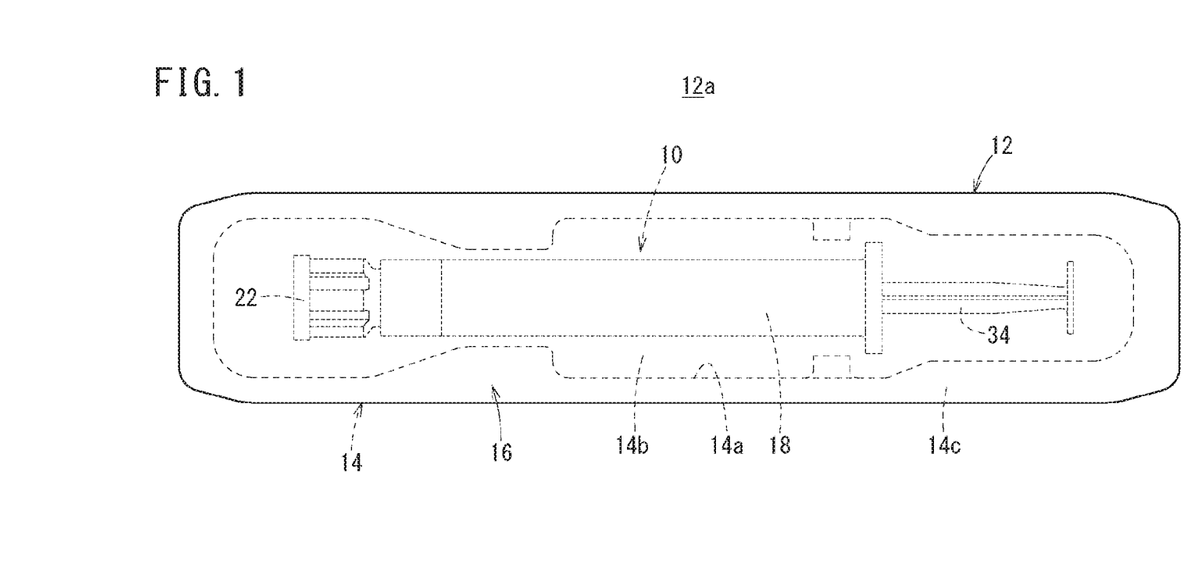
FIG. 1 is a plan view of a package (a prefilled syringe-containing package) in which a prefilled syringe according to a first embodiment is stored.
Figure 2:
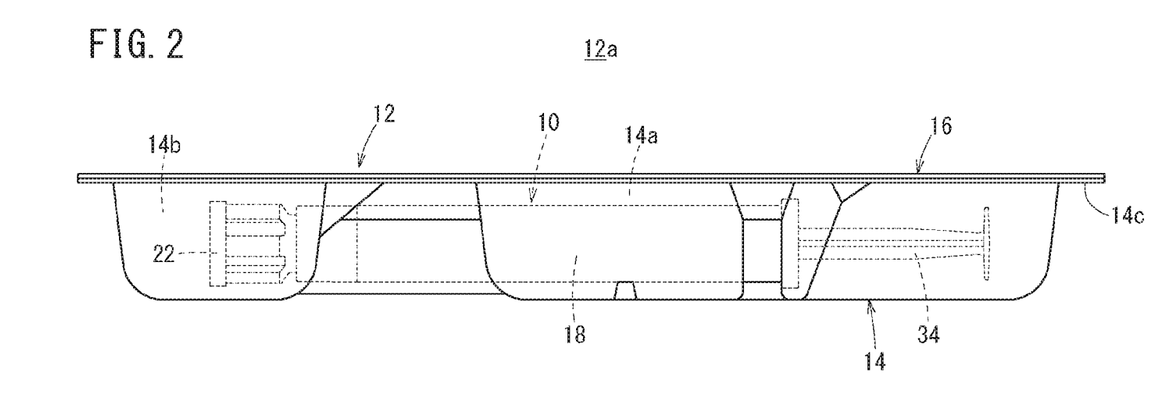
FIG. 2 is a side view of the prefilled syringe-containing package illustrated in FIG. 1.

In FIGS. 1 and 2, a prefilled syringe 10 according to the present embodiment is accommodated in a package 12. The package 12 includes a container body 14 that accommodates the prefilled syringe 10 and a sealing film 16 that seals an opening 14a of the container body 14 in an openable manner. The package 12 illustrated in FIG. 1 is a blister package. The package 12 may be a bag-shaped package that can be sealed and opened. Hereinafter, the package 12 accommodating the prefilled syringe 10 will be referred to as a "prefilled syringe-containing package 12a".

The container body 14 includes an accommodating recess 14b capable of accommodating the prefilled syringe 10 and formed in such a shape that suppresses movement of the prefilled syringe 10 and an overhang 14c formed around an upper end of the accommodating recess 14b. The sealing film 16 is peelably attached to the overhang 14c. The sealing film 16 is peelably bonded to an upper surface of the overhang 14c over the entire circumference.

It is preferable to use a material that is not easily degenerated by a hydrogen peroxide or ethylene oxide gas as a material of the package 12. In addition, a waterproof material is preferably used as the material of the package 12.

As the material of the container body 14, for example, polyolefin such as polypropylene and polyethylene, vinyl chloride resin, polyester resin, polystyrene/polypropylene resin, polyethylene/ionomer (for example, ethylene-based, styrene-based, fluorine-based)/polyethylene, and the like can be suitably used.

The sealing film 16 has a base film made of, for example, polyethylene and an adhesive resin layer fixed to at least an outer circumferential portion of a lower surface of the base film, and preferably, further has a surface protective layer disposed on an upper surface of the base film.

Figure 3:
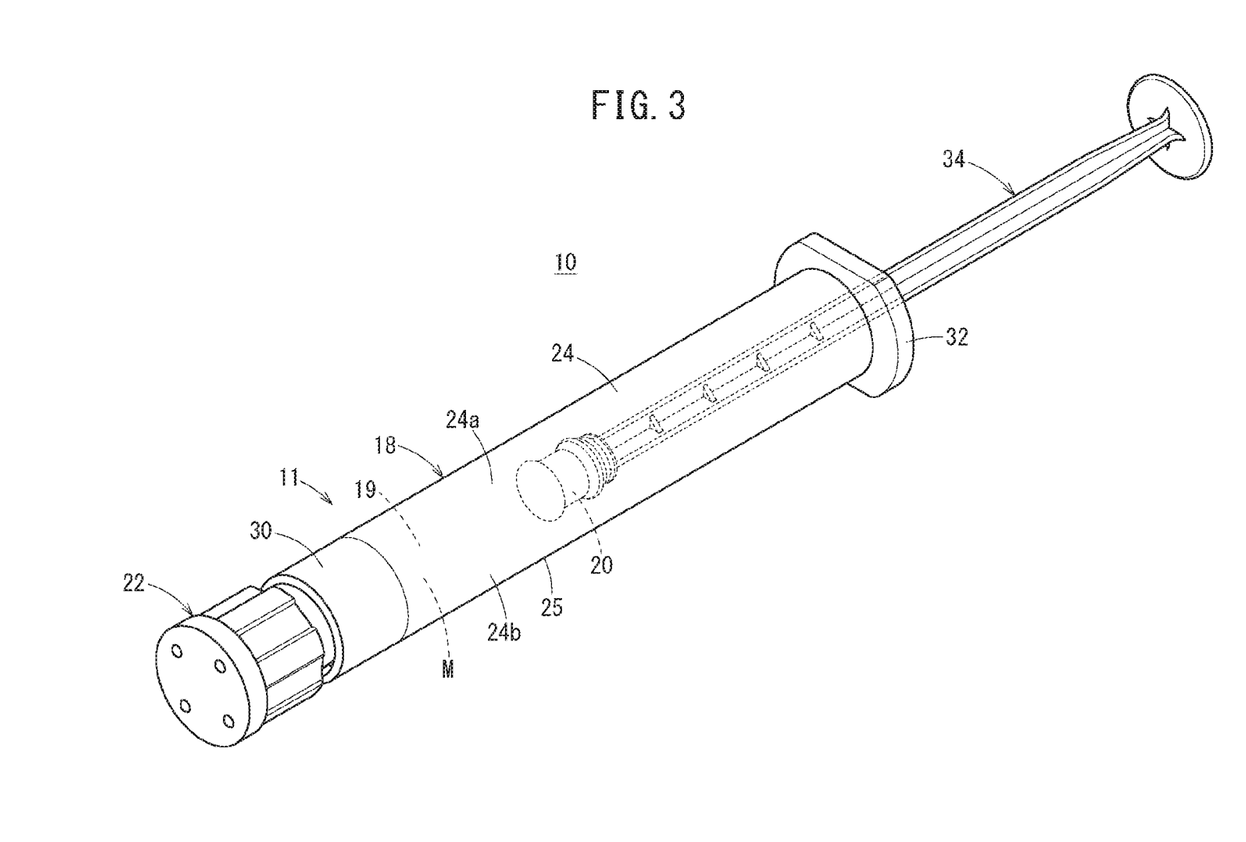
FIG. 3 is a perspective view of the prefilled syringe according to the first embodiment.

As illustrated in FIG. 3, the prefilled syringe 10 includes, as main components, a syringe body 18 having a hollow portion, a gasket 20 slidably inserted into the syringe body 18, a cap 22 sealing a distal-end nozzle 28 (see FIG. 4) of the syringe body 18, and a drug solution M filling a filling space 19 formed by the syringe body 18 and the gasket 20. The syringe system 11 for the prefilled syringe 10 includes the syringe body 18, the gasket 20, and the cap 22.

Figure 4:
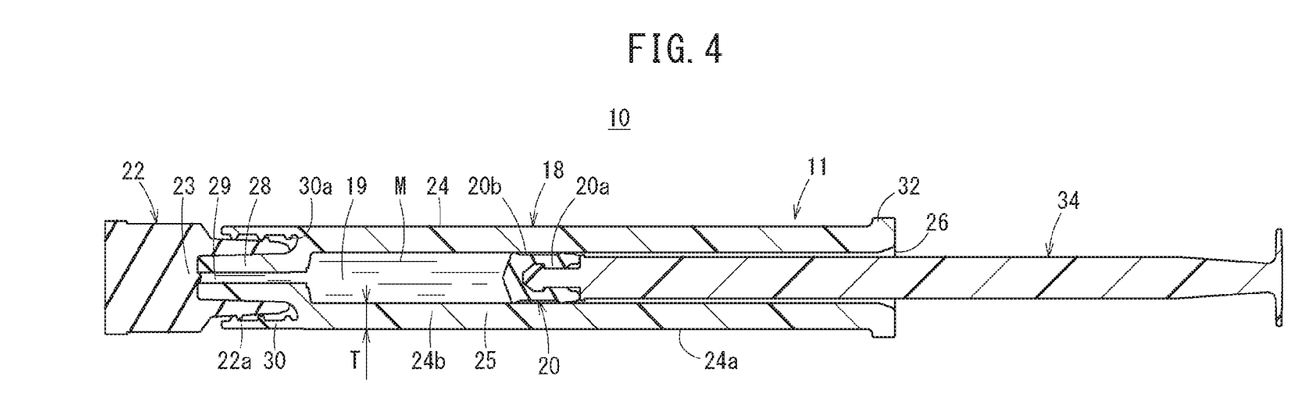
FIG. 4 is a cross-sectional view of the prefilled syringe according to the first embodiment of the present invention.

In FIG. 4, the syringe body 18 has a hollow body portion 24, a proximal-end opening portion 26 disposed at a proximal end portion of the body portion 24, the distal-end nozzle 28 disposed at a distal end portion of the body portion 24, a lock adapter 30 provided outside the distal-end nozzle 28, and a flange 32 formed to protrude radially outward from the proximal end of the body portion 24. In the illustrated syringe body 18, the body portion 24, the distal-end nozzle 28, the lock adapter 30, and the flange 32 are integrally molded. The syringe body 18 is manufactured by, for example, injection molding.

The body portion 24 is formed in a substantially cylindrical shape. The body portion 24 has a side wall 25 extending along the entire circumference in the circumferential direction. The body portion 24 has a thick body portion 24b that accounts for 80% or more of the body portion 24 along the axial direction. A wall thickness T (thickness of the side wall 25) of the thick body portion 24b (excluding the flange 32) is set to be 2.23 to 2.40 mm. There may be a portion outside the above range on a part (for example, the distal end portion or the proximal end portion) of the body portion 24. In particular, in the body portion 24, a wall thickness of a portion filled with at least the drug solution M may be set within the above range, and a wall thickness of a portion on the proximal end side of the portion filled with the drug solution M may be outside the above range. The area of an outer circumferential surface 24a of the body portion 24 is set to be, for example, 1300 to 1600 $mm^2$.

The syringe body 18 is made of a cyclic olefin polymer or a cyclic olefin copolymer. The syringe body 18 may be configured such that at least the body portion 24 is made of the cyclic olefin polymer or the cyclic olefin copolymer and a part other than the body portion 24 is made of another material. A nominal volume of the syringe body 18 is, for example, in a range of 0.1 to 5 mL. The nominal volume of the syringe body 18 is preferably in a range of 0.1 to 0.5 mL.

An outer surface of the syringe body 18 is sterilized with a hydrogen peroxide gas or an ethylene oxide gas.

When the sterilization is performed with the hydrogen peroxide gas, a hydrogen peroxide solution is added into the package 12 in an unsealed state. At that time, the hydrogen peroxide solution may be added after accommodating the prefilled syringe 10 in the container body 14, or the prefilled syringe 10 may be accommodated in the container body 14 after adding the hydrogen peroxide solution. After the package 12 is sealed by adding the hydrogen peroxide, the prefilled syringe-containing package 12a is left for a predetermined time under a condition where the hydrogen peroxide solution gasifies so as to gasify the hydrogen peroxide solution inside the package 12. As a result, the prefilled syringe 10 in the package 12 is sterilized by the hydrogen peroxide gas.

On the other hand, when the sterilization is performed with the ethylene oxide gas, the prefilled syringe 10 is accommodated and sealed in the package 12, and then, the prefilled syringe-containing package 12a is arranged in a sterilization device to supply the ethylene oxide gas around the package 12. At this time, the ethylene oxide gas permeates through the sealing film 16 to enter the package 12. As a result, the outer surface of the prefilled syringe 10 is sterilized with the ethylene oxide gas.

The gasket 20 is inserted through the proximal-end opening portion 26 in the syringe body 18. The gasket 20 has an outer circumference in liquid-tight contact with an inner circumferential surface of the syringe body 18, and is slidably arranged in the syringe body 18. The gasket 20 has a gasket body 20a made of an elastic material such as a rubber material and a fluororesin 20b (coating) disposed on the outer surface of the gasket body 20a.

A distal end portion of a pusher 34 is connected to the gasket 20. When a user presses the pusher 34 in the distal end direction, the gasket 20 slides in the distal end direction inside the syringe body 18. The pusher 34 may be connected to the gasket 20 when the drug solution M is administered to a patient. In addition, the pusher 34 is preferably capable of pressing the gasket 20 in the distal end direction, and may be configured to simply abut on the gasket 20 without being connected to the gasket 20.

The proximal end side of the syringe body 18 is sealed by the gasket 20 in a liquid-tight manner, and the drug solution M is sealed in the syringe body 18. The drug solution M is a medicine containing an active ingredient that is easily oxidized, an emulsion preparation, or a medicine that requires sterilization of the outer surface of the syringe body in order to prevent infection during clinical use. The easily-oxidizable active ingredient contained in the drug solution M is, for example, a protein, a peptide, or a nucleic acid. Specific examples of such an easily-oxidizable active ingredient include a vascular endothelial growth factor inhibitor such as aflibercept, ranibizumab, bevacizumab, and the like, for example. Specific examples of the emulsion preparation include propofol, for example. In addition, examples of the medicine that requires sterilization of the outer surface of the syringe body in order to prevent infection during clinical use include an ophthalmic medicine, antibiotics, anesthetics, and the like.

The distal-end nozzle 28 has a reduced diameter relative to the syringe body 18 from the center of the distal end of the body portion 24 and extends in the distal end direction. The distal-end nozzle 28 has a liquid passage 29 communicating with the filling space 19 in the syringe body 18 and passing through the distal-end nozzle 28 in the axial direction.

In a state in which the cap 22 is detached from the distal-end nozzle 28, a needle unit (not illustrated) can be attached to and detached from the distal-end nozzle 28. The needle unit includes a needle body having a needle tip and a needle hub having a protrusion fixed to a proximal end portion of the needle body and protruding outward. The distal-end nozzle 28 can be tapered to be fit to the inner circumferential portion of the needle hub. At the time of use of the prefilled syringe 10, the cap 22 is unplugged (removed from the distal-end nozzle 28 and the lock adapter 30), and the needle hub of the needle unit is connected to the distal-end nozzle 28 and the lock adapter 30 instead.

The lock adapter 30 illustrated in this example is configured in a substantially hollow cylindrical shape that extends in the distal end direction from the distal end of the body portion 24 and surrounds the distal-end nozzle 28. A female screw portion 30a is formed on an inner circumferential surface of the lock adapter 30. The female screw portion 30a is detachably screwed with a male screw portion 22a disposed on the cap 22 in a mounted state of the cap 22. The female screw portion 30a can be engaged with the protrusion disposed on the needle hub of the needle unit described above in a state in which the cap 22 is detached from the syringe body 18.

The lock adapter 30 illustrated in this example may be integrally formed at a proximal end portion of the distal-end nozzle 28. The lock adapter 30 may be a member that is configured as a separate part from the body portion 24 and the distal-end nozzle 28 and fixed to the syringe body 18 or the distal-end nozzle 28.

The cap 22 is detachably mounted to the distal-end nozzle 28. The cap 22 has a sealing portion 23 that seals a distal end opening portion of the distal-end nozzle 28. The cap 22 in this illustrated example is configured to be attachable to and detachable from the distal-end nozzle 28. In the present embodiment, the sealing portion 23 is made of butyl rubber. The sealing portion 23 may be made of another elastic material (for example, latex rubber, silicone rubber, and the like). The cap 22 is not limited to a configuration in which the whole cap is made of an elastic material, and may have, for example, the sealing portion 23 and a cover portion fixed around the sealing portion 23.

The cap 22 is in liquid-tight contact with a distal end surface of the distal-end nozzle 28 in the state in which the cap 22 is mounted to the distal-end nozzle 28. As a result, the drug solution M does not leak out of the cap 22.

The syringe body 18, the syringe system 11, and the prefilled syringe 10 according to the present embodiment configured as described above have the following effects.

As described above, the body portion 24 of the syringe body 18 is made of the cyclic olefin polymer or the cyclic olefin copolymer, and the wall thickness T of the body portion 24 is in a range of 2.23 to 2.40 mm.

In this manner, the wall thickness T of the thick body portion 24b accounting for 80% or more of the body portion 24 is appropriately 2.23 to 2.40 mm in the syringe body 18, and thus, it is possible to effectively suppress the migration of the sterilizing gas into the syringe body 18. Therefore, even when an active ingredient in the drug solution M filling the syringe body 18 is liable to cause denaturation such as oxidation, it is possible to suppress the denaturation of the active ingredient. In addition, because the wall thickness T of the body portion 24 is not too thick, it is possible to reduce sink marks during molding when molding the syringe body 18 even though the body portion 24 is made of the cyclic olefin polymer or the cyclic olefin copolymer. Because the sink marks during molding are reduced, it is easy to secure proper dimensional accuracy of the syringe body 18, and it is possible to produce the syringe body 18 with sufficient efficiency because an extension of time of a cooling step is avoided. Because 80% or more of the body portion 24 is the thick body portion 24b, it is possible to secure moldability while sufficiently suppressing the migration of a sterilizing medium. The thick body portion 24b preferably accounts for 90% or more of the body portion 24 along the axial direction. As a result, it is possible to further secure the moldability while further suppressing the migration of the sterilizing medium.

The nominal volume of the syringe body 18 is in a range of 0.1 to 5 mL. When the nominal volume is in a range of 0.1 to 5 mL, the amount of drug solution filling the syringe body is small, and it is desirable to minimize the migration of the sterilizing gas into the syringe body 18. Thus, the thickness of the body portion 24 employed in the syringe body is advantageous.

More preferably, the nominal volume of the syringe body 18 is in a range of 0.1 to 0.5 mL. When the nominal volume is in a range of 0.1 to 0.5 mL, the amount of a filling drug solution is extremely small, and it is desirable to minimize the migration of the sterilizing gas into the syringe body 18, and thus, the thickness of the body portion 24 employed in the present invention is particularly advantageous.

The area of the outer circumferential surface 24a of the body portion 24 is in a range of 1300 to 1600 mm$^2$. As the contact area between the sterilizing gas and the outer circumferential surface 24a of the body portion 24 is set to be as small as possible, it is possible to decrease the amount of a sterilizing gas required for sterilizing the outer circumferential surface 24a. As a result, it is possible to decrease the amount of a sterilizing gas migrating into the syringe body 18.

The gasket 20 has the gasket body 20a and the fluororesin 20b disposed on the outer surface of the gasket body 20a. According to this configuration, a gas barrier property is improved by the fluororesin 20b, and the sterilizing gas is less likely to migrate into the syringe body 18.

The sealing portion 23 of the cap 22 is made of the butyl rubber. According to this configuration, it is more difficult for the sterilizing gas to migrate into the syringe body 18 because the butyl rubber has low gas permeability.

The drug solution M is the medicine containing the active ingredient that is easily oxidized, the emulsion preparation, or the medicine that requires sterilization of the outer surface of the syringe body 18 in order to prevent infection during clinical use. When the drug solution M is the medicine or the like, the drug solution M is oxidized or denatured by the sterilizing gas such as the hydrogen peroxide gas and the ethylene oxide gas, and thus, the thickness of the body portion 24 employed in the syringe body is advantageous.

The active ingredient in the drug solution M may be a protein, a peptide, or a nucleic acid. When the active ingredient is any of these materials, the drug solution M is particularly easily oxidized, and thus, the thickness of the body portion 24 employed in the syringe body is advantageous.

Next, a test that has been conducted to confirm the effects of the above-described embodiments will be described.

1. Migration Amount Test

Sample

Fourteen prefilled syringes according to the above-described embodiments were prepared (Example A), and fourteen prefilled syringes not according to the above-described embodiments were prepared (Comparative Example A).

Details of Example A are as follows.
Material of Syringe body: Cyclic Olefin Polymer
Nominal Volume of Syringe body: 0.5 mL
Wall Thickness of Body Portion of Syringe body: 2.39 mm (Inner Diameter of 4.7 mm, Outer Diameter of 9.48 mm)
Gasket: Gasket Body Made of Butyl Rubber and Having Outer Surface Coated with Silicone Resin
Material of Cap: Butyl Rubber
Drug solution: Water for Injection of 0.165 mL Details of Comparative Example A are the same as those of Example A except that a body portion of a syringe body has a wall thickness of 1.24 mm (an inner diameter of 4.7 mm, an outer diameter of 7.18 mm).

Test Method

After accommodating the prepared prefilled syringe in the container body of the blister package, 20 µL of a hydrogen peroxide solution whose concentration was adjusted to 2.0 w/v % was dripped into the container body. After dripping the hydrogen peroxide solution, a sealing film was placed on the container body, and the sealing film was heat-sealed to the container body. Thereafter, a measurement sample of the blister package accommodating the prefilled syringe was stored under conditions of a temperature of about 20° C. and a humidity of 50% RH. The sealing film is made of a multilayer laminate film of polyethylene terephthalate/polyethylene/crosslinked foamed polyethylene (manufactured by Dai Nippon Printing Co., Ltd.). The container body is made of a multilayer laminate film of low-density polyethylene/ionomer/low density polyethylene (manufactured by Dai Nippon Printing Co., Ltd.).

Measurement of Migration Amount of Hydrogen Peroxide

As a measuring instrument, an ORITECTOR M-5 (manufactured by Chiyoda Manufacturing Co., Ltd.) was used. Seven prefilled syringes of Example A were collectively used to set 1.155 mL, and 0.845 mL of an extraction solution was added to make up to 2 mL. A hydrogen peroxide concentration (ppm) of the made-up sample was measured. A sample made up in the same manner was measured for the remaining seven prefilled syringes of Example A. A measurement was carried out by the same procedure for Comparative Example A. During the measurement, a detection value was restored with a dilution ratio of 1.73 times to be set as a measured value. The measurement was conducted on the zero-th day, the third day and the fourteenth day after the dripping of the hydrogen peroxide solution.

Results

Figure 5:
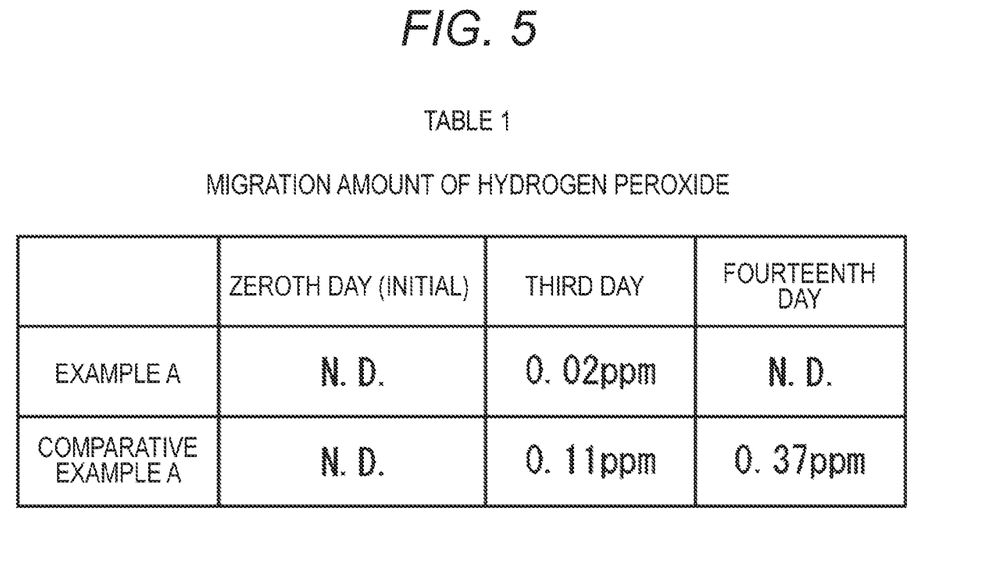
FIG. 5 is Table 1 showing results of a hydrogen peroxide migration amount test.

Measurement results are illustrated in FIG. 5 (Table 1). In Table 1, a measured value is indicated by an average value of two measurements in each of Example A and Comparative Example A. Because a detection limit (lower limit) is 0.01 ppm, "N.D." is expressed, instead of the measured value, when a concentration is less than 0.01 ppm. According to Table 1, it was confirmed that the migration of hydrogen peroxide into the syringe was satisfactorily suppressed in Example A. On the other hand, it was confirmed that the migration amount of hydrogen peroxide into the syringe increased to an unacceptable level in a short period of time (the third day) and the migration amount further increased with the passage of days in Comparative Example A.

Figure 6:
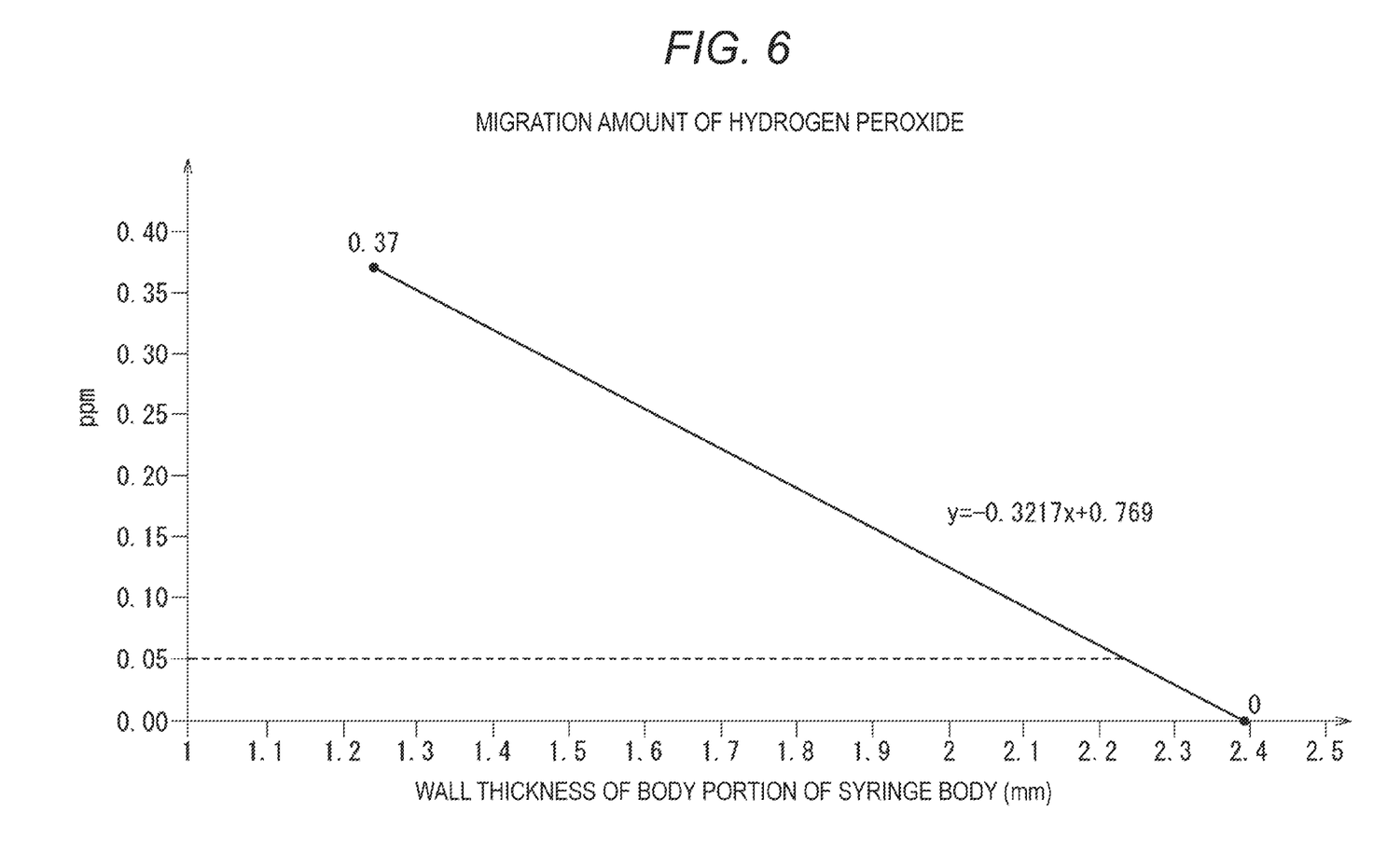
FIG. 6 is a graph illustrating a relationship between a wall thickness of a body portion of a syringe body and a migration amount of hydrogen peroxide.

It is estimated that the relationship between the wall thickness of the body portion of the syringe body and the migration amount of hydrogen peroxide is indicated by a formula ($y=-0.3217x+0.769$) illustrated in FIG. 6 based on results illustrated in Table 1. It is considered that the influence on the drug solution can be sufficiently suppressed when the migration amount is 0.05 ppm or less. The wall thickness of the body portion of the syringe body of 0.05 ppm is 2.23 mm based on the measurement results. Therefore, it is possible to suppress the migration amount to 0.05 ppm or less when the wall thickness of the body portion of the syringe body is 2.23 mm or more.

2. Bacteria Killing Property Test

Sample

A prefilled syringe identical to that of Example A of the migration amount test was prepared.

Test Method

A prefilled syringe, packed in a blister package with dripping of a hydrogen peroxide solution (having the same concentration and amount as those in the migration amount test) into the blister package, was prepared as Example B. In addition, a prefilled syringe, packed in a blister package without dripping of a hydrogen peroxide solution into the blister package, was prepared as Comparative Example B. A biological indicator was placed near a cap. The hydrogen peroxide solution was dripped near a proximal end of a pusher. Example B and Comparative Example B were stored under conditions of a temperature of about 20° C. and a humidity of about 50% RH.

Measurement of Number of Viable Bacteria

The stored samples were taken out on the zero-th day and the fourteenth day after dripping of the hydrogen peroxide solution, and the number of bacteria was measured. At that time, the biological indicator was aseptically removed and 10 mL of a sterilized washing solution (5% of peptone, 0.9% of sodium chloride, 0.1% of Tween 80) was added to extract and collect adhering bacteria. After appropriate dilution using this washing solution as a $10^{-0}$ (1 fold) dilution, the resultant was subjected to pour plate with a TSA agar medium (medium in which 20 g of tryptic soybean was stirred and dissolved with 500 mL of distilled water and autoclaved at 121° C. for 20 minutes) to be cultured at 55° C. for two days. After culturing, the number of appearing colonies was counted. A measurement result was indicated as an average value of five specimens for each of Example B and Comparative Example B.

Results

Figure 7:
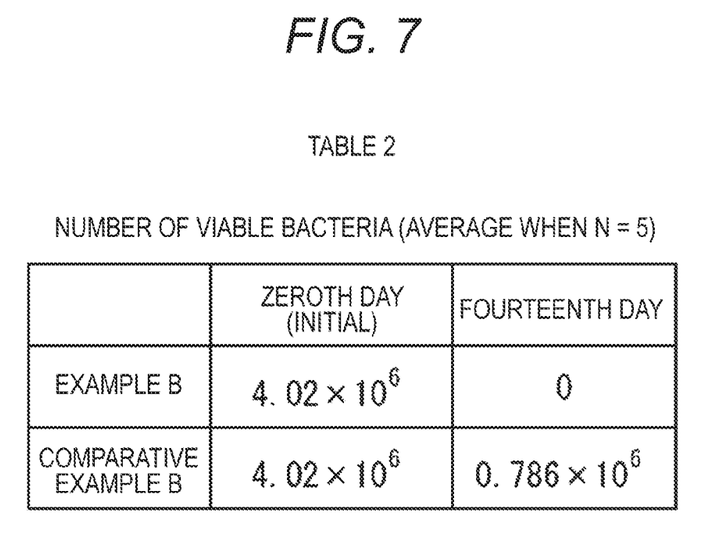
FIG. 7 is Table 2 showing results of a bacteria killing property test.

Measurement results are illustrated in FIG. 7 (Table 2). According to Table 2, viable bacteria of only $4.02\times10^6$ on the zero-th day were completely killed on the fourteenth day in Example B. That is, it is considered that the outer surface of the syringe body was sterilized even if bacteria adhered to the outer surface of the syringe body. On the other hand, it was confirmed that the bacteria were still viable although bacterial reduction was observed on the fourteenth day in Comparative Example B.

It is understood that it is possible to effectively suppress the migration of hydrogen peroxide into the syringe body even when a sufficient amount of hydrogen peroxide was added for sterilization based on the results illustrated in Table 2.

The present invention is not limited to the above-described embodiments, and various modifications can be made within a scope not departing from a gist of the present invention.

What is claimed is:

1. A syringe body for a prefilled syringe, the syringe body comprising:
   a hollow body portion;
   a proximal-end opening portion disposed at a proximal end portion of the body portion; and
   a distal-end nozzle disposed at a distal end portion of the body portion;
   wherein the body portion is made of a cyclic olefin polymer or a cyclic olefin copolymer;
   wherein the body portion includes a thick body portion accounting for 80% or more of the body portion along an axial direction;
   wherein a nominal volume of the syringe body is in a range of 0.1 to 5 mL; and
   wherein a wall thickness of the thick body portion is in a range of 2.23 to 2.40 mm.

2. The syringe body according to claim 1, wherein:
   a nominal volume of the syringe body is in a range of 0.1 to 0.5 mL.

3. The syringe body according to claim 1, wherein:
   an area of an outer circumferential surface of the body portion is in a range of 1300 to 1600 mm².

4. The syringe body according to claim 2, wherein:
an area of an outer circumferential surface of the body portion is in a range of 1300 to 1600 mm².

5. A syringe system for a prefilled syringe, the syringe system comprising:
a syringe body comprising:
a hollow body portion,
a proximal-end opening portion disposed at a proximal end portion of the body portion, and
a distal-end nozzle disposed at a distal end portion of the body portion
wherein the body portion is made of a cyclic olefin polymer or a cyclic olefin copolymer,
wherein a nominal volume of the syringe body is in a range of 0.1 to 5 mL, and
wherein a wall thickness of the body portion is a range of 2.23 to 2.40 mm;
a gasket that is slidably disposed in the body portion; and
a cap comprising a sealing portion sealing an opening portion of the distal-end nozzle.

6. The syringe system according to claim 5, wherein:
a nominal volume of the syringe body is in a range of 0.1 to 0.5 mL.

7. The syringe system according to claim 5, wherein the gasket includes a gasket body, and a fluororesin disposed on an outer surface of the gasket body.

8. The syringe system according to claim 5, wherein:
the sealing portion of the cap is made of butyl rubber.

9. A prefilled syringe comprising:
a syringe body comprising:
a hollow body portion
a proximal-end opening portion disposed at a proximal end portion of the body portion, and
a distal-end nozzle disposed at a distal end portion of the body portion,
wherein the body portion is made of a cyclic olefin polymer or a cyclic olefin copolymer,
wherein a nominal volume of the syringe body is in a range of 0.1 to 5 mL, and
wherein a wall thickness of the body portion is in a range of 2.23 to 2.40 mm;
a gasket that is slidably disposed in the body portion;
a cap comprising a sealing portion sealing an opening portion of the distal-end nozzle; and
a drug solution that is filled in a filling space formed by the syringe body and the gasket;
wherein an outer surface of the syringe body is sterilized with a hydrogen peroxide or ethylene oxide gas.

10. The prefilled syringe according to claim 9, wherein:
a nominal volume of the syringe body is in a range of 0.1 to 0.5 mL.

11. A prefilled syringe comprising:
a syringe body comprising:
a hollow body portion,
a proximal-end opening portion disposed at a proximal end portion of the body portion, and
a distal-end nozzle disposed at a distal end portion of the body portion,
wherein the body portion is made of a cyclic olefin polymer or a cyclic olefin copolymer,
wherein a nominal volume of the syringe body is in a range of 0.1 to 5 mL, and
wherein a wall thickness of the body portion is in a range of 2.23 to 2.40 mm;
a gasket that is slidably disposed in the body portion;
a cap comprising a sealing portion sealing an opening portion of the distal-end nozzle; and
a drug solution filled in a filling space formed by the syringe body and the gasket;
wherein the outer surface of the syringe body is a surface that has been sterilized with a hydrogen peroxide or ethylene oxide gas.

12. The prefilled syringe according to claim 11, wherein:
the drug solution is a medicine that contains an active ingredient comprising at least one of: a protein, a peptide, and/or a nucleic acid.

13. The prefilled syringe according to claim 12, wherein:
a nominal volume of the syringe body is in a range of 0.1 to 0.5 mL.

* * * * *